United States Patent [19]
Ryu

[11] Patent Number: 5,986,157
[45] Date of Patent: Nov. 16, 1999

[54] PROCESS FOR THE REMOVAL OF CARBONYL COMPOUNDS IN ISOMERIZATION FEED STREAMS

[75] Inventor: J. Yong Ryu, League City, Tex.

[73] Assignee: Catalytic Distillation Technologies, Pasadena, Tex.

[21] Appl. No.: 09/018,110

[22] Filed: Feb. 3, 1998

[51] Int. Cl.$^6$ ............................ C07C 5/22; C07C 5/27
[52] U.S. Cl. .................... 585/671; 585/809; 585/820
[58] Field of Search .................... 585/671, 820, 585/809

[56] References Cited

U.S. PATENT DOCUMENTS

| | | | |
|---|---|---|---|
| 3,449,436 | 6/1969 | O'Connor et al. | 260/593 |
| 3,453,343 | 7/1969 | Holiday | 260/676 |
| 4,358,362 | 11/1982 | Smith et al. | 208/91 |
| 4,814,517 | 3/1989 | Trubac | 568/697 |
| 5,118,871 | 6/1992 | Cikut et al. | 568/697 |
| 5,210,327 | 5/1993 | Luebke et al. | 568/697 |
| 5,276,212 | 1/1994 | Luebke et al. | 568/697 |
| 5,283,373 | 2/1994 | Luebke et al. | 568/697 |
| 5,300,696 | 4/1994 | Luebke et al. | 568/697 |

*Primary Examiner*—Walter D. Griffin
*Assistant Examiner*—Thuan D. Dang
*Attorney, Agent, or Firm*—Kenneth H. Johnson

[57] ABSTRACT

Carbonyl compound contaminants are removed from hydrocarbon streams containing olefins for use, for example, in the process for the skeletal isomerization of olefins by pretreating the hydrocarbon stream by passing it over an acidic catalyst at elevated temperatures in the range of 100–400° C. under conditions to react the carbonyls to form reaction products which are deposited onto the catalyst.

10 Claims, 2 Drawing Sheets

PROCESS FOR THE REMOVAL OF CARBONYL COMPOUNDS IN ISOMERIZATION FEED STREAMS

BACKGROUND OF THE INVENTION

1. Field of the Invention

The present invention relates generally to a process for the removal of carbonyl contaminants in hydrocarbon streams. More particularly the invention relates to the removal of carbonyl compounds from a stream containing at least aldehydes, ketones or esters. More particularly the invention relates to a removal process wherein the carbonyl compounds, including the aldehydes and ketones, undergo reactions in the presence of an acidic catalyst and at least, a part of the reaction products are adsorbed/absorbed on the catalyst.

2. Related Art

Linear olefins are isomerized to branched olefins in the presence of an acidic catalyst such as molecular sieves, silica-alumina, fluorinated alumina, etc. The tertiary olefins that are a product of the isomerization are useful as feed to a tertiary ether process or to an alkylation process.

When a stream containing both linear and branched olefins is fed to an etherification process the branched olefins preferentially react with an alcohol to produce the tertiary ether. In the case of isobutene and methanol the reaction product is methyl tertiary butyl ether (MTBE) and in the case of isopentene (isoamylene) and methanol the product is tertiary amyl methyl ether (TAME). Both ethers are useful as gasoline additives.

The unreacted linear olefins, either the normal butenes or normal pentenes, can be used in a cold acid alkylation process or may be isomerized to branched olefins and recycled back to the etherification process. In either case, the normal olefins from the initial etherification may contain trace amounts of the unreacted alcohol which act as catalyst inhibitor in the isomerization process or consume acid in cold acid alkylations. Aldehydes and ketones may be contained in other feedstreams to a skeletal isomerization process. For example, the $C_5$ stream from a Fischer-Tropsch synthetic fuel process contains small amounts of acetone, propionaldehyde, methyl ethyl ketone and butylaldehyde as well as alcohols. These carbonyl compounds render molecular sieve skeletal isomerization catalysts, such as zeolites, e.g., ferrierite, useless after only a few hours on stream. In an integrated process for etherification and isomerization as disclosed in U.S. Pat. Nos. 5,210,327 and 5,276,212, the linear olefins are treated to remove the alcohol, water and nitrogen compounds prior to the isomerization. The alcohol and nitrogen compounds are removed by adsorption on zeolitic molecular sieves by a process disclosed in U.S. Pat. No. 4,814,517. Any acetone or acetonitrile in the feed is removed by a water wash prior to the etherification.

SUMMARY OF THE INVENTION

In the present process the carbonyl compounds, comprising at least aldehydes or ketones, contact the acidic material at a temperature high enough to cause the reaction of the carbonyl compounds on contact with the acidic material and adsorption onto the acidic material which is regenerated or replaced after the acidic material declines in activity.

One embodiment of the present invention comprises a process for treating feeds to an olefin isomerization process to remove the carbonyl compounds in which a feed stream comprising a mixed hydrocarbon stream containing linear and branched $C_5$ olefins along with small amounts of aldehydes, ketones and alcohols. The feed is passed over an acidic catalyst, such as τ-alumina at moderately elevated temperatures in vapor phase to react the carbonyl compounds with themselves and the olefins. At least a part of the reaction products are deposited onto the alumina and the feed is then passed over an olefin skeletal isomerization catalyst to convert linear olefins to branched olefins. Some of the reaction products may stay on the acidic material or desorb into hydrocarbon vapor phase, depending on the temperature of the acidic material catalyst bed, molecular weight of reaction products and type of the reaction products whether olefins, olefinic alcohols or diols. Particularly the normal pentenes are converted to isoamylenes.

As used herein the term "adsorbed" and its variations mean a physical intervention of the sorbed material into the absorbent without chemical change of the absorbed material and hence condensed phase (multimolecular layers) can be formed on the surface of solid materials such as vapor condensation on a solid surface. "Adsorbed" and its variations mean a bonding of the sorbed material onto the surfaces of the adsorbent (chemisorption) and hence chemisorption does not go beyond the formation of a monolayer on the surface.

DESCRIPTION OF THE PREFERRED EMBODIMENTS

Figure 1:
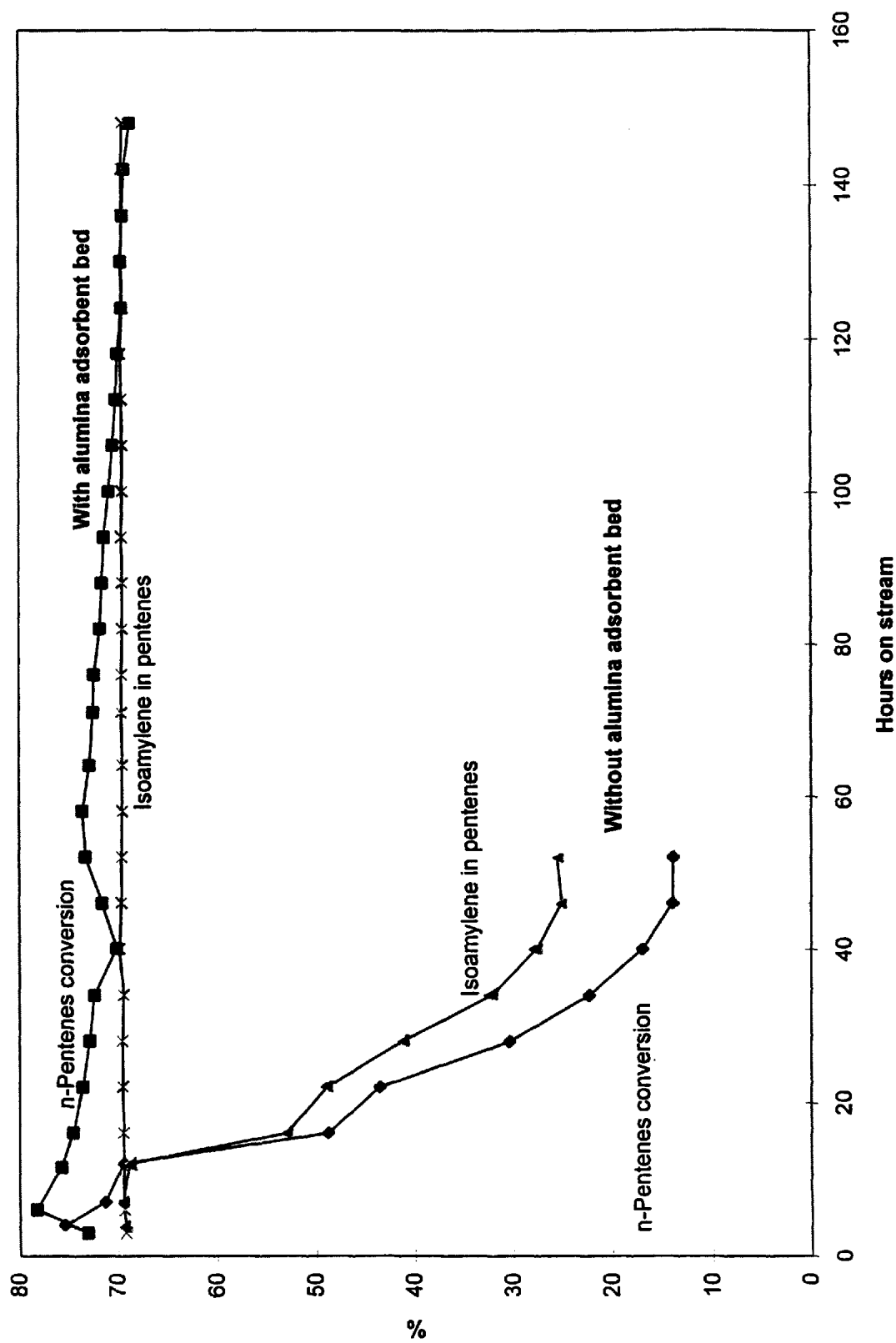
FIG. 1 is a plot of n-Pentene conversion and isoamylene in pentenes versus time on stream for a skeletal isomerization process with and without pretreatment of the feed.

The carbonyl compounds include aldehydes and or ketones which are reactive compounds and hence undergo various reactions in the presence of acidic catalysts. Acid catalyzed condensation of aldehydes and ketones produces dimers, oligomers, and polymers. Also aldehydes and ketones can be added to olefins in the presence of acid catalyst to produce alcohols, olefins or allylic type alcohols depending on the structure of the olefins and the reaction temperature. A very small amount of these aldehydes, e.g., ketones and/or aldehydes, in the hundreds of parts per million, or generally less than 0.1 weight percent, are contained in various feed stocks which would otherwise be considered choices for skeletal isomerization of the olefins contained therein. Such feed stocks especially include naphtha from a synthetic fuel process such as Fischer-Tropsch. However, even these minor amounts cause rapid deactivation of the isomerization catalyst.

The catalysts useful in the invention are alumina, silica alumina, acidic metal oxides, mixed metal oxides, molecular sieves, clays, salts of weak base and strong acids. The preferred acidic materials are acidic clays, calcined bauxite and high surface area alumina such as τ, δ, ∩, Θ, p-aluminas, silica modified alumina and slightly fluorinated aluminas. By the term "high surface" area is meant greater than 10 square meters per g. The acidic material may be one material, a mixture of acidic materials or discrete beds of one or more acidic materials.

In the preferred embodiment the olefin containing stream is pretreated by passing it over a bed of τ alumina at about 100–400° C. and from 0–20 psig pressure at weight hourly space velocities of from 0.5 $h^{-1}$ to about $10^{-h}$ (WHSV= weight hourly space velocity=weight of feed per hour per weight of catalyst). This results in almost complete removal of the aldehydes and ketones. It is believed that the aldehydes and ketones are removed by reacting with themselves or with olefins.

Depending on the reaction temperature and molecular weights of the reaction products, at least a portion of the reaction products is deposited on the τ alumina catalyst. Therefore the catalyst gradually loses its activity due to the deposited materials and has to be regenerated or replaced. The regeneration of the deactivated catalyst can be done by burning off the deposited material at an elevated temperature (450–700° C.). In the alternative the spent catalyst may be regenerated by washing with an aromatic solvent such as toluene or ethers such as MTBE or TAME at warm temperatures (35–200° C.) and drying at elevated temperatures (200–400° C.). In the present invention the acidic materials, sorbents, act as both absorber and adsorber. In the prior processes the presence of ketones and/or aldehydes in the feed streams was not disclosed.

The treated stream can be passed on to a skeletal isomerization process utilizing a typical isomerization catalyst, such as ferrierite, at isomerization conditions, typically about 400° C., 5–50 psig and 1–10 WHSV (weight hourly space velocity =weight of feed per hour per weight of catalyst).

EXAMPLE 1

For comparison purposes ferrierite catalyst (6.9 g of 3/16" trilobes) was loaded in a stainless steel tubular reactor (0.5" ID×10" length) and activated at 260° C. in nitrogen gas flow for five hours. Normal pentenes in a mixed $C_5$ feed, which contained 648 wppm 2-methyl ethyl ketone, 718 wppm n-propanal, 65.3% n-pentenes, 2.6% 3-methyl-1-butene, 9.7% isoamylenes (2-methyl-1-butene+2-methyl-2-butene), and 285 wppm $C_4$–$C_5$ total dienes, were isomerized at 400° C., 7 psig, and 7 WHSV. The test results (the conversion of n-pentenes and content of isoamylenes in $C_5$ olefins) are shown in FIG. 1. The conversion declined from about 76% at the beginning to less than 15% in just 43 hours. The content of isoamylenes in pentenes declined from about 69% to about 25% in the same period.

EXAMPLE 2

The identical isomerization to Example 1 was carried out using the same feed and catalyst, except that the feed was passed through an alumina bed prior to introducing it to the reactor. Sixty-five grams of τ-alumina (1/16" diameter spheres, 193 m²/g/surface area, and 0.93 cc/g pore volume) was loaded into a stainless steel tubular reactor (1" ID×12" length) and activated at 450° C. in nitrogen gas flow. The feed was passed through the τ-alumina at about 167° C. and then introduced to the isomerization reactor. At six hours on stream analysis of a sample of the effluent from the τ-alumina bed indicated that all the carbonyl compounds (methyl ethyl ketone and n-propanal) were completely removed. The isomerization results are also in FIG. 1 for 148 hours on stream. The isomerization catalyst performance was dramatically improved. The catalyst deactivation rate was only about 1% conversion drop per day and the content of isoamylenes in the pentenes remained constant at about 69.5% throughout the test period. After shut down, a visual inspection of the spent alumina spheres indicated the deposition of a yellowish material on the catalyst.

EXAMPLE 3

Figure 2:
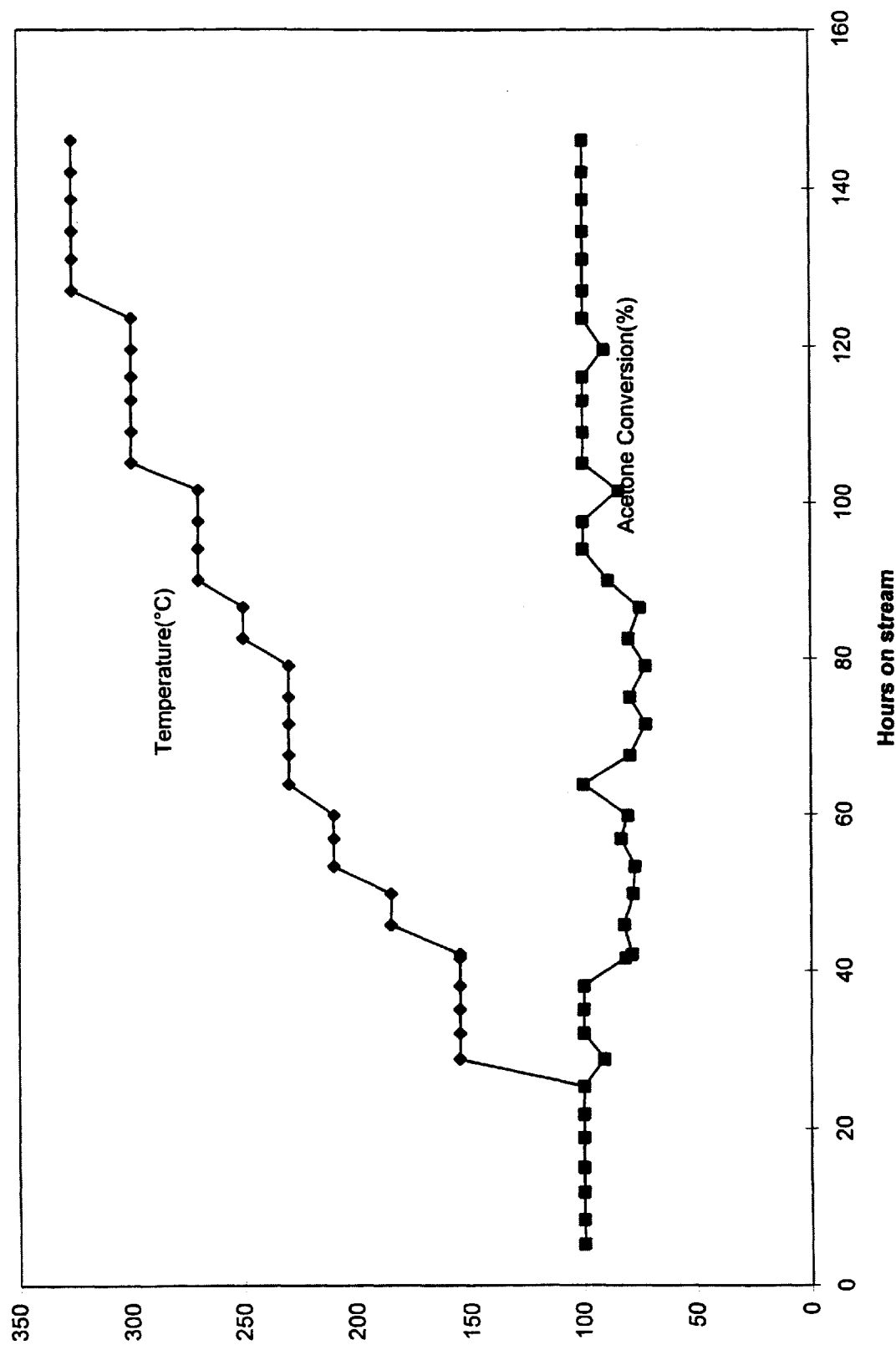
FIG. 2 is a plot of acetone conversion and reactor temperature versus time on stream for another carbonyl compound containing feed stream being treated over a τ-alumina catalyst.

A feed was prepared containing 748 wppm acetone and 187 wppm MTBE in a mixed $C_5$ hydrocarbon stream (29.2% 2methyl-2-methyl-2butene, 1% t-2-pentene, 0.4% c-2-pentene, 65.8% isopentane and 3.5% others). The feed was passed through a bed of τ-alumina to remove acetone at increasing temperatures off from 100–326° C. and 10 psig. The feed rate was changed during the run as follows: 1.18 WHSV for the first 12 hours, 1.77 WHSV for the next 7 hours, 2.36 WHSV for the next 6 hours, and 2.95 WHSV for the rest of the run. The run was terminated at 146 hours. The temperature was increased to keep the acetone conversion at 100%. The results are shown in FIG. 2.

The invention claimed is:

1. In a process for the skeletal isomerization of olefins, a hydrocarbon stream containing carbonyl compounds comprising at least ketones and aldehydes, the improvement comprising pretreating said hydrocarbon stream by passing said hydrocarbon stream over an acidic catalyst is selected from the group consisting of alumina, acidic metal oxides, mixed metal oxides, molecular sieves, clays and salts of weak base and strong acids under conditions sufficient to react said carbonyl compounds to form reaction product and deposit said reaction product on said acidic catalyst.

2. The process according to claim 1 comprising passing said mixed hydrocarbon stream over a bed of acidic catalyst at 100–400° C., 0.5–10 WHSV, and 0–20 psig pressure.

3. The process according to claim 1 wherein said acidic catalyst is selected from the group consisting of acidic clays, calcined bauxite and high surface area alumina.

4. The process according to claim 3 wherein said acidic catalyst consists of τ-alumina.

5. A process for the skeletal isomerization of normal olefins contained in a mixed hydrocarbon stream containing ketones and aldehydes, comprising:

(a) pretreating said hydrocarbon stream by passing said hydrocarbon stream over an acidic catalyst at conditions sufficient to react substantially all of said ketones, and aldehydes to form reaction products wherein the reaction products are deposited upon said acidic catalyst; and (b) passing said pretreated hydrocarbon stream over a skeletal isomerization catalyst at skeletal isomerization conditions wherein a portion of said normal olefins are isomerized to branched olefins.

6. The process according to claim 5 wherein said acidic catalyst comprises τ-alumina and said isomerization catalyst comprises ferrierite.

7. The process according to claim 5 wherein said acidic catalyst and said isomerization catalyst are contained in separate reactors.

8. The process according to claim 5 wherein said normal olefins comprise normal pentene and said normal pentenes are skeletally isomerized to 2-methyl-1-butene and 2methyl-2-butene.

9. The process according to claim 5 for the skeletal isomerization of normal pentenes contained in a mixed hydrocarbon stream containing ketones, aldehydes and esters comprising:

(a) pretreating said hydrocarbon stream by passing said hydrocarbon stream over an acidic τ-alumina catalyst at from 100–400° C. to react substantially all of said ketones, aldehydes and esters with themselves or a portion of the olefins wherein the reaction product are deposited upon said acidic catalyst; and (b) passing said pretreated hydrocarbon stream over a ferrierite catalyst under isomerization conditions wherein a portion of said normal pentenes are isomerized to 2-methyl-1-butene and 2-methyl-2-butene.

10. The process according to claim 9 wherein said τ-alumina catalyst and said ferrierite catalyst are contained in separate reactors.

* * * * *